United States Patent [19]

Grunder et al.

[11] 4,272,868

[45] Jun. 16, 1981

[54] DEVICE FOR OBTAINING A CONTROL SIGNAL CORRESPONDING TO THE DENSITY OF THE FIBRE WEB LYING ON A FIBRE-CARRYING ELEMENT OF A CARD

[75] Inventors: Werner Grunder, Mönchaltorf; Ernst Loch, Uster, both of Switzerland

[73] Assignee: Zellweger Uster, Ltd., Uster, Switzerland

[21] Appl. No.: 33,448

[22] Filed: Apr. 26, 1979

[30] Foreign Application Priority Data

Apr. 26, 1978 [CH] Switzerland .................... 4496/78

[51] Int. Cl.³ ............................................. D01H 5/38
[52] U.S. Cl. ........................................ 19/240; 19/98; 19/105; 19/106 R
[58] Field of Search .................. 19/0.2, 0.23, 0.24, 19/0.25, 98, 105, 106 R, 239, 240

[56] References Cited

U.S. PATENT DOCUMENTS

| 2,980,967 | 4/1961 | Munford et al. | 19/0.23 |
| 3,441,984 | 5/1969 | Bryan et al. | 19/0.23 |
| 3,644,964 | 2/1972 | Varga | 19/240 |

FOREIGN PATENT DOCUMENTS

| 2658044 | 6/1978 | Fed. Rep. of Germany | 19/240 |
| 2704241 | 8/1978 | Fed. Rep. of Germany | 19/240 |

Primary Examiner—Louis Rimrodt
Attorney, Agent, or Firm—Craig and Antonelli

[57] ABSTRACT

A device for obtaining a control signal corresponding to the density of the fibre covering lying on a fibre carrying element such as the cylinder, the licker-in, the take-off roller, or the doffer of a card. The device includes a holder which extends over the width of the fibre carrying element to span the width of the fibre covering on the fibre carrying element. This holder contains means responsive to the density of the fibre covering which produces electric output signals corresponding to the density of the fibre covering.

28 Claims, 5 Drawing Figures

DEVICE FOR OBTAINING A CONTROL SIGNAL CORRESPONDING TO THE DENSITY OF THE FIBRE WEB LYING ON A FIBRE-CARRYING ELEMENT OF A CARD

CROSS-REFERENCE TO RELATED APPLICATION

The present application is related to application Ser. No. 033,477 entitled "A METHOD AND APPARATUS FOR REGULATING OUT VARIATIONS IN THE SLIVER WEIGHT ON DEVICES FOR PROCESSING FIBRE SLIVERS," filed on Apr. 26, 1979 herewith by Werner Grunder, which discloses a method and apparatus which the measurement device of the present invention can be used in conjunction with.

BACKGROUND OF THE INVENTION

This invention relates to a device for obtaining a control signal corresponding to the density of a fibre web lying on the cylinder of a carding machine.

The production of fibre slivers having cross-sections which are as uniform as possible represents a pressing problem in the textile industry. In particular, the fibre material should be measured with respect to its cross-section at an early stage where regulators for correcting undesirable deviations can be inserted using relatively simple means.

Various devices for measuring the cross-section of card slivers are already known and used. In order to allow the cross-section of the sliver and the sliver count to be regulated with as little delay as possible, there have been attempts to determine the amount of fibre at a location which is as near as possible to the position where the fibre material is metered in. On a card having a take-in regulator, it is the feed roller which simultaneously forms the regulating position. The feed roller charges the cylinder with fibre material via a licker-in. It is very convenient to measure, by means of the feed roller, the fibre covering of the cylinder from the viewpoint of determining the momentary fibre feed with as little delay as possible.

However, because of the structural design of a card there are only a few possible positions for a measuring device. It is particularly aggravating that the fibre material on the cylinder is finely distributed over its entire width, that the cylinder rotates at a relatively high speed, that its circumferential speed is high and that its surface is rough. The arrangement of a measuring device is also complicated by the fact that the cylinder is a very close fit in a housing and the aerodynamic conditions between cylinder surface and housing should not be disturbed. Up until now, all of these aggravating circumstances have made it impossible to provide a reliable measuring device which is both insensitive to the rough operating conditions and suitable for the requirements of regulation.

Optical measuring devices are known but are not suitable for protecting the entire width of the fibre covering and are not, therefore, suitable as measuring devices for regulating the cross-section of the sliver.

It is also known to make use of a pneumatic measuring device which utilizes the pressure differences in the cylinder housing caused by the fibre covering of the cylinder. However, the device needs several measuring positions on the circumference of the cylinder and is not suitable for measurement on the licker-in, the doffer or the take-off rollers.

SUMMARY OF THE INVENTION

An object of the present invention is to provide a measuring device for producing a control signal which is accurate for regulation purposes even under rough operating conditions.

To accomplish this and other objects, the invention provides an apparatus for obtaining a control signal corresponding to the density of the fibre covering lying on the cylinder, the licker-in, the take-off roller, or the doffer of a card. The apparatus comprises a holder which extends over the entire width of the cylinder, the licker-in, the doffer, or the take-off rollers, and which contains means responsive to the density of the fibre covering, said means being arranged to provide electric signals corresponding to the density of the fibre covering.

DETAILED DESCRIPTION OF THE INVENTION

Preferred embodiments of the invention will now be discussed with reference to the drawings wherein the same numerals are used throughout the figures to identify elements common to different embodiments.

Figure 1:
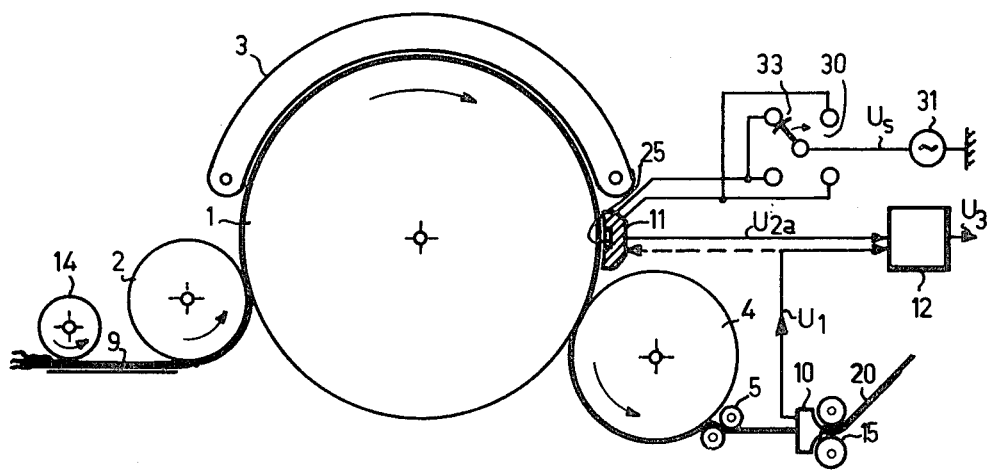
FIG. 1 diagrammatically illustrates a card with an additional measuring device according to the present invention.

The card illustrated in FIG. 1 is known per se and basically comprises a cylinder 1, a licker-in 2, laps 3, a doffer 4 and take-off rollers 5. Fibre material 9 is supplied by a feed roller 14 which is connected to the licker-in 2. The take-off rollers 5 are followed by calender rollers 15 which convey the sliver 20. The sliver is condensed in a funnel. This funnel can be constructed as a first measuring device 10 for the cross-section of the sliver 20 which measuring device 10 can be constructed in a manner known in the art.

An additional measuring device 11 for determining the density of the fibre covering on the cylinder 1 is arranged between the laps 3 and the doffer 4 or at another suitable position on the card. The measuring device 11 is supplied with the necessary feed voltage $U_s$ from a feed voltage source 31 via a switching device 30. A test signal $U_2$ obtained in this way is emitted as a component $U_3$ via an amplifier 12 wherein $U_3$ represents the unknown density being measured. If the design of the card permits it, the measuring device 11 can also be arranged at another position along the path of the fibre covering, for example, between the licker-in 2 and the laps 3, or even on the licker-in 2, the doffer 4, or the take-off rollers 5.

Figure 2:
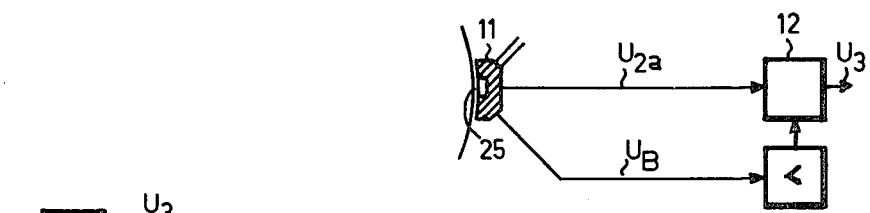
FIG. 2 shows a detail of an electrical circuit used in conjunction with a measuring device.

The first measuring device 10 emits a control signal $U_1$ for controlling the amplifier 12. FIG. 2 shows diagrammatically control of the degree of amplification of the amplifier 12 by means of a reference signal $U_B$ obtained in the additional measuring device 11.

Figure 3:
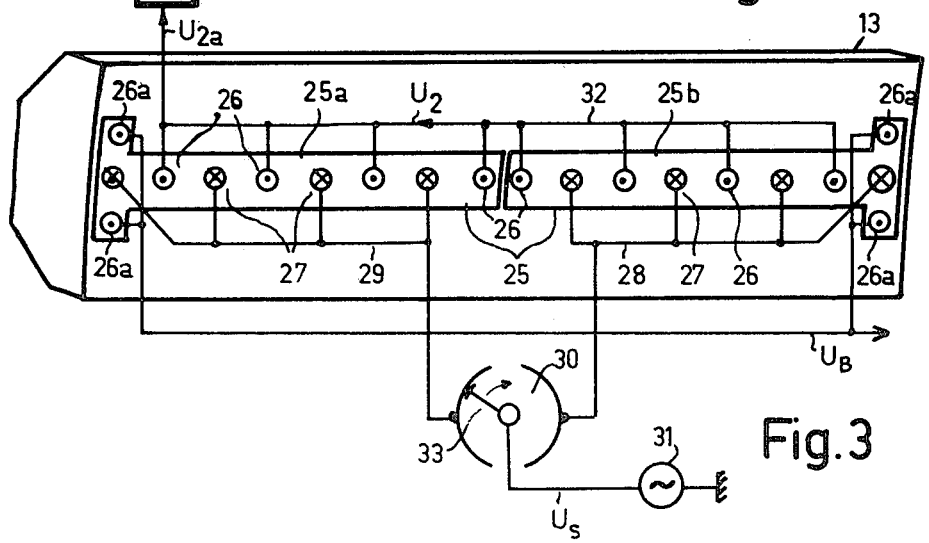
FIG. 3 illustrates a measuring device in accordance with the present invention.

FIG. 3 shows the additional measuring device 11 in detail. The device comprises a holder 13 which extends over the entire width of either the cylinder 1, the licker-in 2, the doffer 4, or the take-off rollers 5. A transparent rail 25 which forms a step-less face with the holder 13 is inserted on its side facing the fibre covering. This prevents fibre material from being deposited on discontinuities of the face.

Light transmitters 27 and light receivers 26 which can be constructed of known elements are inserted alternately into the transparent rail 25 and are joined by bus bars 28, 29, 32. The transparent rail 25 can be provided, for increasing the yield of light in the direction of the fibre covering 9, with reflecting coverings 19. Light transmitters and light receivers are preferably operated in the infrared range of the spectrum. The light transmitters 27 of the left-hand half of the rail 25a and those of the right-hand half of the rail 25b are advantageously combined and coupled, via the bus bars 28 and 29 to a switching device 30. A rotor 33 of this switching device 30 connects the feed voltage source 31 alternately via the bus bars 28 and 29 in such a way that the left-hand half of the light transmitters 27 does not irradiate any light when the right-hand half of the light transmitters is irradiating light, and vice versa. In addition to electrical advantages, this resolves the test signal in a better way than with continuous modulation of the light transmitters 27.

The light receivers 26 which emit the test signals $U_2$ are fed via a bus bar 32 which guides the test signal $U_2'$ to an amplifier 12. The amplifier 12 emits the component $U_3$ representing the unknown density being measured. Additional light receivers 26' can also be arranged in the rail 25, and their object is described below.

Figure 4:
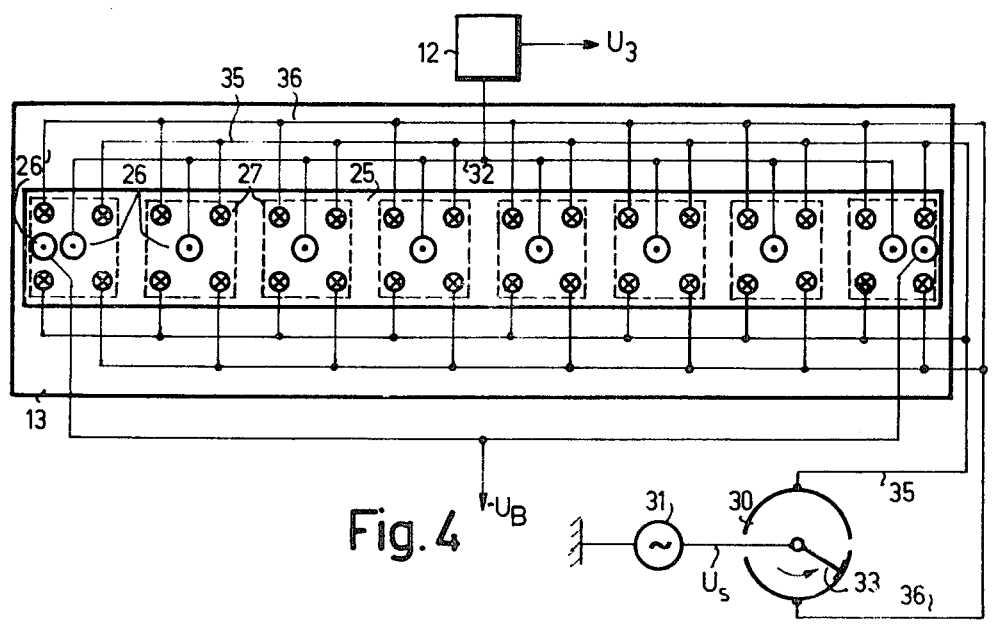
FIG. 4 is a view of a modified measuring device in accordance with the present invention.

In a modification of this embodiment illustrated in FIG. 4, the light receivers 26 are each surrounded by several, preferably four, light transmitters 27. They are located, for example, in the corners of a square conceived as a center about the light receivers 26. This should allow the fibre material to be illuminated from various directions in order to achieve uniform reflection and thus an improved signal yield if the fibres are insufficiently parallel.

The light transmitters 27 are connected in parallel in pairs by means of feed voltage bus bars 35 and 36. The switching device 30 distributes the feed voltage $U_s$ alternately to two opposing light transmitters 27 each by means of the rotor 33. The fibre material is thus exposed from two directions which are off-set by 90°.

The switch-over device 30, 33 can be an electronic switch, in which case bus bars and the switching device can be fitted in the holder 13.

Since only relative changes in the density of the fibre covering 9 on the cylinder, the licker-in 2, the doffer 4, or on the take-off rollers 5 are obtained as an output signal $U_3$, a reference value for the magnitude of this output signal or for the degree of amplification of the amplifier 12 should be introduced. The test signal $U_1$ of the first measuring arrangement 10 can be used for this purpose in a first embodiment by feeding it to the amplifier 12 to control the magnitude for the degree of amplification of the amplifier 12. On the one hand, this may make changes in the light yield from the light transmitters 27 and the light receivers 26 ineffective. On the other hand, the magnitude of the output signal $U_3$ is correlated with the magnitude of the absolute count of the fibre sliver 20.

Another means for controlling the degree of amplification of the amplifier 12 involves the production of a reference signal $U_B$ at a point on the rail 25, preferably in the region of the edge zones of either the cylinder 1, the licker-in 2, the doffer 4, or the take-off rollers 5 which supports practically no fibre covering, by means of at least one additional light receiver 26'. The magnitude of this reference signal is dependent only on the reflecting properties of the surface of the cylinder, the licker-in, the doffer or the take-off rollers, and, therefore, is capable of forming a control magnitude for the amplifier 12.

Another manner of changing the relationship between changes of the fibre covering and the output signal $U_3$ involves controlling the intensity of the output signals $U_2$, for example, by controlling the intensity of light from the light transmitters 27. In this case, it is also possible to use the signals $U_1$ or $U_B$ as control magnitudes, as discussed above.

Figure 5:
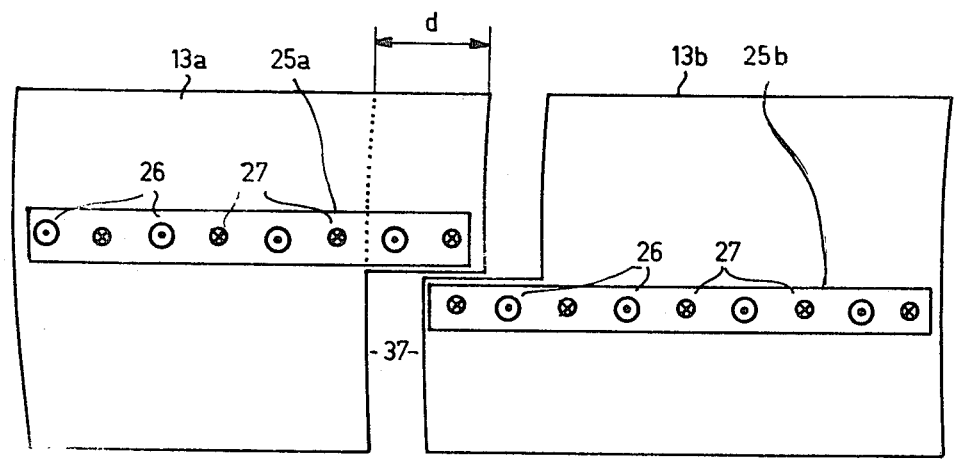
FIG. 5 illustrates a structural detail of an adjustable holder in accordance with the present invention.

A particular problem for measuring devices which extend over the entire width of the machine is their varying width. It should not be necessary to keep a measuring device produced to size ready for each machine. According to a development of the device according to the invention, this is solved by designing the holder 13 with the transparent rail 25 in two parts, the central portions of which overlap. FIG. 5 shows this diagrammatically. The halves of the holders 13a, 13b can be drawn apart by the distance d. The electric members for signal production and signal evaluation remain unchanged in this embodiment.

While we have shown and described several embodiments in accordance with the present invention, it is understood that the same is not limited thereto but is susceptible of numerous changes and modifications as known to a person skilled in the art, and we therefore do not wish to be limited to the details shown and described herein but intend to cover all such changes and modifications as are obvious to one of ordinary skill in the art.

We claim:

1. A device for obtaining a control signal corresponding to the density of the fibre covering lying on a fibre carrying element of a card, comprising:
    a holder which extends over the width of the fibre carrying element to span the width of the fibre covering on said fibre carrying element; and
    means mounted on said holder responsive to the density of the fibre covering lying on the fibre carrying element for producing output signals corresponding to the density of the fibre covering.

2. A device according to claim 1, further comprising:
    light transmitters and light receivers arranged in the holder to extend over the width of the fibre covering on said fibre carrying element so that light irradiated from at least one portion of the light transmitters is reflected by the fibre covering located on the fibre carrying element and is converted into corresponding electric output signals by the light receivers; and
    means for combining the output signals from at least one portion of the light receivers to produce a resulting output signal.

3. A device according to claim 2, wherein the light transmitters and light receivers are mounted on a transparent rail facing the fibre carrying element.

4. A device according to claim 3, wherein the transparent rail is so arranged in the holder as to form a stepless face with it.

5. A device according to claims 3 or 4, wherein at least the lateral faces of the transparent rail are arranged to reflect to the interior of the rail.

6. A device according to claims 1, 2, or 3, wherein the output signals are pulse signals.

7. A device according to claim 3, wherein the transparent rail is divided into two portions, and a changeover switch is provided so that the light transmitters of one portion and the light transmitters of the other portion can alternately emit light.

8. A device according to claims 2 or 3, wherein the light transmitters are arranged in groups with each group of transmitters surrounding one light receiver, wherein the light transmitters in each group are excited to emit light in a cyclic sequence.

9. A device according to claims 2 or 3, wherein four light transmitters are arranged around each light receiver.

10. A device according to claim 9, wherein each light receiver lies in the center of four light transmitters which are spaced at the corners of a square arrangement surrounding the receiver.

11. A device according to claim 10, further comprising a switch operable so that the respective opposing light transmitters can alternately emit light.

12. A device according to claim 2, further comprising means for controlling the intensity of the luminous flux from the light transmitters.

13. A device according to claim 12, further comprising means for supplying a control signal for controlling the intensity of the luminous flux wherein said control signal corresponds to the absolute sliver count.

14. A device according to claim 12, further comprising means for supplying a control signal for controlling the intensity of the luminous flux wherein said control signal corresponds to the absolute variations in the sliver count.

15. A device according to claims 13 or 14, wherein the means for supplying a control signal comprises a reference light receiver arranged in the region of one of the light transmitters and being operable optically to scan a portion of the fibre carrying element which is free from fibre covering.

16. A device according to claim 2, further comprising means for controlling the intensity of the luminous flux from the output signals from the light receivers.

17. A device according to claim 16, further comprising means for supplying a control signal for controlling the intensity of the luminous flux wherein said control signal corresponds to the absolute sliver count.

18. A device according to claim 16, further comprising means for supplying a control signal for controlling the intensity of the luminous flux wherein said control signal corresponds to the absolute variations in the sliver count.

19. A device according to claims 17 or 18, wherein the means for supplying a control signal comprises a reference light receiver arranged in the region of one of the light transmitters and being operable optically to scan a portion of the fibre carrying element which is free from fibre covering.

20. A device according to claims 1 or 2, comprising an adjustable amplifier arranged to receive the output signals.

21. A device according to claim 20, wherein the amplification of the amplifier can be controlled by the control signal responsive to the absolute sliver count.

22. A device according to claim 20, wherein the amplification of the amplifier can be controlled by the control signal responsive to the absolute variations in the sliver count.

23. A device according to claim 20, comprising means for supplying to the amplifier a control signal which is derived from the reference light receiver.

24. A device according to claims 1, 2, or 3, wherein the holder has two parts which slidably overlap one another so that the holder can be adapted to various widths of cylinders or licker-ins or doffers or take-off rollers.

25. A device according to claims 1 or 2, wherein the fibre carrying element is a cylinder of the card.

26. A device according to claims 1 or 2, wherein the fibre carrying element is licker-in of the card.

27. A device according to claims 1 or 2, wherein the fibre carrying element is a doffer of the card.

28. A device according to claims 1 or 2, wherein the fibre carrying element is a take-off roller of the card.

* * * * *